United States Patent [19]

Harwood et al.

[11] Patent Number: 5,387,414
[45] Date of Patent: Feb. 7, 1995

[54] RECOMBINANT ANTICOCCIDIAL VACCINE

[75] Inventors: David E. Harwood; Glenda Hamby, both of Fayetteville, Ark.

[73] Assignee: British Technology Group USA Inc., Gulph Mills, Pa.

[21] Appl. No.: 43,760

[22] Filed: Apr. 7, 1993

Related U.S. Application Data

[63] Continuation of Ser. No. 667,293, Mar. 14, 1991, abandoned.

[51] Int. Cl.$^6$ ............ C07K 13/00; C12R 1/90; A61K 35/68; A61K 39/012
[52] U.S. Cl. ............ 424/191.1; 435/69.3; 435/258.4; 514/2; 530/350; 530/822; 424/267.1
[58] Field of Search ............ 424/88; 435/69.3, 258.4; 514/2; 530/350, 822; 536/23.1

[56] References Cited

U.S. PATENT DOCUMENTS 4,710,377 12/1987 Schenkel ............ 424/88

OTHER PUBLICATIONS

Lamont, et al., (1990) "Immunogenetics," in Crawford, ed., Poultry Breeding and Genetics, Elsevier, N.Y., Chapter 22, pp. 497–541.
Danforth, et al., "Study of an *Escherichia Coli* Elicited Avian Coccidial Protein", J. Cell. Biochem., Suppl. 10A, p. 146, Abst. C89 (1986).
Johnson, et al., "Anticoccidial Drugs: Lesion Scoring Techniques in Battery and Floor-Pen Experiments with Chickens", Experimental Parasitology, 28:30–36 (1970).
Danforth, et al., "Development of an Avian Coccidial Antigen by Recombinant DNA Technology", Poultry Science, 64:85 (1985).
Wisher, Martin H., "Identification of the Sporozoite Antigens of *Eimeria tenella*", Molecular and Biochemical Parasitology, 21:7–15 (1986).
Danforth, et al., "Use of Hybridoma Antibodies and Recombinant DNA Technology in Protozoan Vaccine Develoment", Avian Diseases, 30:37–42 (1986).
Clarke, et al., "Isolation of λamp3 Genomic Recombinants Coding for Antigens of *Eimeria tenella*", Molecular and Biochemical Parasitology, 22:79–87 (1987).
Jenkins, et al., "*Eimeria acervulina*: DNA Cloning and characterization of Recombinant Sporozoite and Merozoite Antigens", Experimental Parasitology, 66:96–107 (1988).
Kim, et al., "Immunization of Chickens with Live *Escherichia coli* Expressing *Eimeria acervulina* Merozoite Recombinant Antigen Induces Partial Protection Against Coccidiosis", Infection and Immunity, 57:2423–2440 (1989).
Wallach, et al., "*Eimeria maxima*: Identification of Gametocyte Protein Antigens", Experimental Parasitology, 68:49–56 (1989).
Miller, et al., "Characterization and Vaccine Potential of a Novel Recombinant Coccidial Antigen" Infection and Immunity, 57:2014–2020 (1989).
Menscher, et al., "Antigenic Proteins of *Eimeria maxima* Gametocytes: Cell-Free Translation and Detection with Recovered Chicken Serum", Experimental Parasitology, 68:40–48 (1989).
Wallach, et al., "Passive Immunization of Chickens Against *Eimeria maxima* Infection With a Monoclonal Antibody Developed Against a Gametocyte Antigen", Infection and Immunity, 58:557–562 (1990).
Takahashi, et al., "Selective Breeding for High and Low Antibody Responses to Inactivated Newcastle (List continued on next page.)

*Primary Examiner*—Robert A. Wax
*Assistant Examiner*—Dian C. Jacobson
*Attorney, Agent, or Firm*—Banner, Birch, McKie & Beckett

[57] ABSTRACT

An anti-coccidial vaccine is provided which contains a recombinant peptide with novel epitopes. The recombinant peptide has an amino-terminal amino acid sequence that is unique among known Eimeria antigens. Recombinant vectors encoding the novel peptide antigen are deposited under ATCC Accession No. 68450, and ATCC Accession No. 68537.

8 Claims, No Drawings

OTHER PUBLICATIONS

Disease Virus in Japanese Quails", Poultry Science, 63:595–599 (1984).

Edison, et al., "Performance of Broiler Progeny of Breeder Flocks Vaccinated with Inactivated Oil Emulsion Malabsorption Syndrome Virus Vaccine", Poultry Science, 64:2081–2086 (1985).

Schwan, et al., "Binding of Chicken, Bovine, and Rabbit Immunoglobulins by Avian, Bovine, and Human Strains of *Staphylococcus aureus*", Poultry Science, 65:696–703 (1986).

Clarke, et al., "DNA Sequences Coding for Antigens of Eimeria Tenella Cloned and Expressed in Escherichia Coli", in Molecular Strategies of Parasitic Invasion, proceedings of a MacArthur Foundation–UCLA Symposium, Park City, Utah, Jan. 1987, published by Alan R. Liss, Inc., New York, 1987, pp. 701–711.

Wisher, et al., "*Eimeria tenella* Sporozoites: The Method of Excystation Affects the Surface Membrane Proteins", Parasitology, 95:479–489 (1987).

McDonald, et al., "*Eimeria tenella:* Immunological Diversity Between Asexual Generations", Parasite Immunology, 10:649–660 (1988).

Sutton, et al., "Characterization of Coccidial Proteins by Two–Dimensional Sodium Dodecyl Sulphate–Polyacrylamide Gel Electrophoresis", Parasitology, 99:175–187 (1989).

Danforth, et al., "Genetically Engineered Antigen Confers Partial Protection Against Avian Coccidial Parasites", Poultry Science, 68:1643–1652 (1989).

Flexner, Charles, "New Approaches to Vaccination", Advances in Pharmacology, 21:51–99 (1990).

Clarke, et al., "Regions of an *Eimeria tenella* Antigen Contain Sequences Which Are Conserved In Circumsporozoite Proteins from *Plasmodium spp.* and Which are Related to the Thrombospondin GenelFamily", Molecular and Biochemical Parasitology, 41:269–280 (1990).

Heller, et al., "Serological Evidence for Major Histocompatibility Complex (B Complex) Antigens in Broilers Selected for Humoral Immune Response", Poultry Science, 70:726–732 (1991).

Leitner, et al., "Replicated Divergent Selection of Broiler Chickens for High or Low Early Antibody Response to *Escherichia coli* Vaccination", Poultry Science, 71:27–37 (1992).

Clarke, et al., "Antigens of Eimeria Cloned and Expressed in *E. Coli.*", Journal of Cell. Biochem., Suppl. 10A, p. 145, Abst. C87 (1986).

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i i i ) HYPOTHETICAL: N ( v ) FRAGMENT TYPE: N-terminal ( v i ) ORIGINAL SOURCE:
        ( A ) ORGANISM: Eimeria maxima ( v i i ) IMMEDIATE SOURCE:
        ( B ) CLONE: rPV1-89

( x i ) SEQUENCE DESCRIPTION: SEQ ID NO:1:

```
Xaa  Glu  Gln  Glu  Thr  Ser  Ala  Thr  Glu  Val  Xaa  Thr  Pro  Ser  Tyr  Lys
 1                   5                        10                       15

Met  Thr  Xaa  Ser
             20
```

RECOMBINANT ANTICOCCIDIAL VACCINE

This application is a continuation of application Ser No. 07/667,293, filed Mar. 14, 1991 now abandoned.

FIELD OF THE INVENTION

This invention relates to anticoccidial vaccines containing recombinant peptide immugens.

BACKGROUND OF THE INVENTION

Coccidiosis is a widespread disease of acute economic concern to the poultry industry. The invasive intestinal infection is caused by one or more of several species of Eimeria that invade the digestive tract of birds, causing depressed weight gain, intestinal and cecal lesions, depigmentation and poor feed conversion. Economic losses to the poultry industry from this disease have been estimated to be as high as $300 million annually (Danforth, H. D., and P. C. Augustine. 1985, "Use of hybridoma antibodies and recombinant DNA technology in protozoan vaccine development," Avian Diseases, 30:37–42). Current coccidiostatic and coccidiocidal medications to combat this disease add another $100 million in annual production costs to the poultry industry. Due to evidence of increasing resistance to currently marketed anticoccidial drugs, immunological techniques to create a vaccine against the parasites are being investigated by various groups.

Certain regions on the cell surface of the coccidial parasite have been shown to possess discrete immunogenic properties (Danforth, et al., 1985). Because subunit techniques have proved to be a successful method of inducing partial or complete immunity against a variety of antigens, the molecular manipulation of Eimeria immunogenic regions to induce an immune response in the host has been tested as an anti-coccidial approach.

Due to the logistical difficulties inherent in the isolation of native Eimeria cell surface proteins in sufficient quantities to permit characterization and testing for vaccine efficacy, workers have utilized the biotechnological isolation of the gene(s) coding for these antigenic proteins to produce mass quantities of recombinant antigenic protein in host bacterial or yeast cells. Recombinant anticoccidial vaccines are currently under study by numerous groups. Most of these vaccines have demonstrated the ability to reduce intestinal lesions or oocyst excretion in challenge studies. While similar recombinant techniques and procedures were employed by these workers to synthesize each of the proteins, each vaccine may be differentiated with statistical certainty based on the amino acid sequences of the different recombinant immunogens.

Danforth, et al., (1985) discloses a recombinant coccidial protein which provides partial protection against coccidial infection by a particular Eimeria species. The article does not teach that the protein provides cross-protection against other coccidial species.

Kim et al., 1989, Infection and Immunity, vol. 57, pp. 2434–40, teaches cloned p250 surface antigen of Eimeria acervulina merozoites. Upon inoculation with transformed E. coli carrying the cloned antigen, partial protection was achieved. The plasmid carrying the cloned antigen gene survived in the intestinal flora, even after the E. coli which initially harbored the plasmid were no longer present.

Miller, 1989, Infection and Immunity, vol. 57,pp. 2014–20, discloses a cloned protein from Eimeria tenella which was identified using an antibody raised against E. acervulina sporozoites. Live recombinant E. coli harboring the gene for the cloned protein provided a degree of partial protection.

Clarke, et al., 1989, Molecular and Biochemical Parasitology, vol. 22, pp. 79–87, reports the identification of a substantial number of DNA sequences (24), coding for antigens of E. tenella, by direct screening of genomic libraries with immune serum. No protective effects were reported for any of these antigens.

Australian Patent Application of Merck & Co., A U-A28542/89 discloses E. tenella recombinant protein immunogens. The sequence of at least one such immunogen is disclosed.

Australian Patent Application A U-A-65869/86 of Solvay and Cie, discloses a cloned antigen which confers immunity against Eimeria tenella, Eimeria necatrix and Eimeria maxima. The antigen comprises two polypeptides joined by a disulfide bond and having molecular weights of about 17,000 and 8,000, respectively.

International Patent Application No. WO 90/00403 of Genex Corporation discloses a cloned gene encoding an antigenic protein found in avian coccialia. Seven different sequences are disclosed which are immunoreactive with antibodies against coccialia.

European Publication No. 0 349 071 of Akzo N.V. discloses a polypeptide of Eimeria which can be used to immunize poultry. Molecular clones were isolated from both E. acervulina and E. tenella.

European Publication No. 0 344 808 of F. Hoffman la Roche AG discloses cloned antigem for protection against coccidiosis. Sequences of the antigens are disclosed.

European Publication No. 0 324 648 of Merck & Co. discloses cloned genes coding for Group A, C, F, and H Eimeria tenella immunogens.

SUMMARY OF THE INVENTION

It is an object of this invention to provide a vaccine against coccidiosis which contains a peptide immunogen comprising novel epitopes.

It is a further object of this invention to provide a simple and efficient method of producing the immunogen.

It is an additional object of this invention to provide a method for preventing coccidiosis in chickens.

This invention provides a vaccine composition comprising an immunogenic peptide produced by expression of a recombinant DNA sequence corresponding to the DNA sequence inserted in the unique EcoRI site of the lambda gt11 bacteriophage deposited under ATCC Accession Number 68450, or alternatively, the DNA sequence inserted at the unique pBR322 EcoRI site in the recombinant bacterial plasmid deposited under ATCC Accession No. 68537, or a peptide containing epitopes encoded by these sequences.

This invention also provides a method for producing peptide immunogens having the desired epitopes, comprising transforming a host cell with a DNA molecule comprising a DNA sequence encoding a peptide whose amino acid sequence corresponds to the peptide encoded by the DNA sequence inserted in the unique lambda gt11 EcoRI site in recombinant bacteriophage deposited under ATCC Accession Number 68450, or alternatively, the DNA sequence inserted at the unique pBR322 EcoRI site in the recombinant bacterial plasmic deposited under ATCC Accession No. 68537, and growing the transformed cell so that the DNA sequence is expressed.

This invention further provides an intron-free DNA sequence encoding a novel peptide which is specifically immunoreactive with antibodies produced by chickens infected with Eimeria species and which contains the amino acid sequence disclosed in SEQ ID NO:1.

This invention additionally provides procedures for vaccinating chickens against coccidiosis comprising administering the vaccine of this invention to the chickens.

A cDNA sequence has been isolated and cloned from *Eimeria maxima* messenger RNA which codes for an immunogenic protein containing one or more antigenic determinants that produce a coccidiocidal and/or coccidiostatic effect when used for vaccination in the bird. As compared to existing vaccines, this vaccine has improved efficacy as well as cross reactivity against more than one species of Eimeria.

DETAILED DESCRIPTION OF THE INVENTION

The practice of the present invention employs, unless otherwise indicated, conventional molecular biology, microbiology, and recombinant DNA techniques within the skill of the art. Such techniques are explained fully in the literature. See, e.g., Sambrook, et. al., "Molecular Cloning: A Laboratory Manual" (1989); "DNA Cloning: A Practical Approach," Volumes I and II (D. N. Glover, ed., 1985); "Oligonucleotide Synthesis" (M. J. Gait, ed., 1984); "Nucleic Acid Hybridization (B. D. Hames & S. J. Higgins, eds., 1984, "Transcription and Translation" (B. D. Hames & S. J. Higgins, eds., 1984); "Animal Cell Culture" (R. I. Freshney, ed., 1986); "Immobilized Cells and Enzymes" (IRL Press, 1986); B. Perbal, "A Practical Guide to Molecular Cloning" (1984).

Definitions

In describing the present invention, the following terminology is used in accordance with the definitions set out below.

"Recombinant DNA" is a DNA molecule which includes DNA sequences obtained from two or more species.

One DNA sequence "corresponds" to another DNA sequence if the two sequences encode the same amino acid sequence.

One amino acid sequence "corresponds" to another amino acid sequence if at least 75% of the amino acid positions in the first sequence are occupied by the same amino acid residues in the second sequence. Preferably 90% of the amino acid positions are identical, and most preferably 95% of the amino acid positions are identical. Alternatively, two amino acid sequences are considered to correspond to each other if the differences between the two sequences involve only conservative substitutions.

"Conservative amino acid substitutions" are the substitution of one amino acid residue in a sequence by another residue of similar properties, such that the secondary and tertiary structure of the resultant peptides are substantially the same. Amino acid pairs which may be conservatively substituted for one another are well-known to those of ordinary skill in the art.

Peptides are specifically immunoreactive with a particular antibody if they bind to the antigen binding site of the particular antibody.

"Immunogenic peptides," when injected into animals cause those animals to develop the ability to produce antibodies which are specifically immunoreactive with the peptides.

"Cross-reactive peptides" are peptides that compete for the same antigenic binding site. If binding of one peptide to an antibody prevents binding by a second peptide, then the two peptides are cross-reactive.

"Substantially pure peptide" according to the invention is one which is virtually free of other coccidial peptides. Most simply this can be accomplished by expression of the coccidial protein of the present invention in a recombinant host cell. Alternatively, the antibodies of the present invention can be used to immunoaffinity purify the coccidial protein of the present invention.

The DNA Sequence

The present invention concerns a vaccine against coccidiosis which contains an immunogenic recombinant peptide having hitherto unknown epitopes which are cross-reactive with epitopes on many Eimeria species. The invention provides transformed cells containing a DNA sequence encoding the recombinant peptide.

A cDNA sequence encoding the immunogenic peptide of the vaccine was first obtained by isolating messenger RNA from the sporozoite state of Eimeria coccidia. The messenger RNA was used as a template for reverse transeriptase to create cDNA. The cDNA was digested with a restriction endonuelease, EcoRI, and shotgun cloned into a plasmid vector, pBR322. Competent bacterial cells, *E. coli* HB101, were then transformed with this cloning vector. Alternatively, EcoRI-digested cDNA was ligated into the EcoRI site of lambda gt11 bacteriophage, and *E. coli* Y1088 or Y1090 were transformed with this vector. Transformant colonies were plated on selective media and those containing the desired cDNA sequence were identified with polyclonal antisera from birds exposed to Eimeria oocyst infection. The positive clones were amplified and tested for the presence of the recombinant protein by Western blot analysis. One positive clone, isolated from a pBR322 library, contains cDNA encoding a recombinant peptide which exhibits hitherto unknown epitopes it was designated rPV1-89 and deposited with the American Type Culture Collection (ATCC) under ATCC Accession No. 68537. Another such clone, isolated from a lambda gt11 library, was designated rBP1-2 and has been deposited under ATCC Accession No. 68450. DNA sequences encoding the immunogenic peptide of this invention can be isolated from EcoRI digests of the deposited clones.

Clones containing the DNA sequence of this invention can be obtained by those of ordinary skill in the art using well-known procedures. For instance, a library of Eimeria DNA sequences may be constructed in any convenient vector (see, e.g., Sambrook, et al.), and then clones can be selected which hybridize with the cDNA sequence isolated from rBP1-2 or rPV1-89. Alternatively, a family of DNA probes representing degenerate sequences encoding SEQ ID NO: 1 may be constructed, and clones from the library selected on the basis of hybridization with these probes. Preferably, DNA from the selected clones should be subcloned into an expression vector, and the protein expressed by cells transformed with the vector should be tested for immunoreactivity with antibodies against the recombinant protein of this invention prepared as described below or for immunoreactivity with sera from birds exposed to Eimeria infection as described above. Such subcloning is easily within the skill of the ordinary worker in the art in view of the present disclosure. Clones expressing immunoreactive recombinant peptides may be used to prepare vaccines as taught below. The amino acid coding region of the DNA sequence of this invention may be longer or shorter than the coding region of the deposited vectors, so long as the recombinant peptide expressed by the DNA sequence retains at least one epitope cross-reactive with antibodies which are specifically immunoreactive with the Eimeria peptide produced by the deposited strains. The preparation of selected clones which contain DNA sequences corresponding to all or part of the sequence of rBP1-2 or rPV1-89 may be accomplished by those of ordinary skill in the art using conventional molecular biology techniques along with the information provided in this specification and, optionally, the transformed cells deposited under ATCC Accession No. 68450 and ATCC Accession No. 68537.

The Recombinant Protein

The recombinant Eimeria protein encoded by rBP1-2 or by rPV1-89 was isolated from bacterial cells of the positive transformant colonies and purified by ammonium sulfate fractionate and ion exchange chromatography. The recombinant Eimeria protein has an approximate molecular weight of 45-65 kilodaltons, as determined by polyaerylamide gel electrophoresis in sodium dodecyl sulfate (SDS-PAGE). The recombinant protein of this invention has an amino-terminal amino acid sequence which corresponds to the sequence listed as SEQ ID NO: 1. This amino-terminal sequence is different from that of all other known Eimeria proteins, indicating that the DNA sequence inserted in the deposited clones encodes a peptide unknown to the prior art.

The purified recombinant protein was administered to birds free of the specific pathogen, and the birds were later challenged with various species of Eimeria. This vaccination with the recombinant protein protected the birds from a wide range of Eimeria species. The recombinant protein reacts with antibodies which are specifically immunoreactive with, for example, E. tenella, E. mitis, E. maxima, E. brunetti, E. acervulina, and E. praecox. Thus the peptide of this invention is a novel immunogen, broadly cross-reactive with surface proteins found on many Eimeria species, in contrast to previously available peptide immunogens which generally react with only one species.

Polypeptides corresponding to the recombinant protein of this invention may be obtained by transforming cells with an expression vector containing DNA from a clone selected from an Eimeria library as described above. Suitable expression vector and host cell systems are well known to those of ordinary skill in the art, and are taught, for instance, in Sambrook, et al., 1989. The peptide may be obtained by growing the transformed cells in culture under conditions wherein the cloned DNA is expressed. Of course, the peptide expressed by the clone may be longer or shorter than the rBP1-2 peptide or the rPV1-89 peptide, so long as the peptides are cross-reactive. Depending on the expression vector chosen, the peptide may be expressed as a fusion protein or a mature protein, secreted or retained intracellularly or as an inclusion protein. The desired polypeptides can be recovered from the culture by well-known procedures, such as centrifugation, filtration, extraction, and the like, with or without cell rupture, depending on how the peptide was expressed. The crude aqueous solution or suspension may be enriched for the desired peptide by protein purification techniques well known to those skilled in the art. Preferred methods are shown in the Examples.

Antibodies Specific for the Recombinant Protein

Antibodies which are specifically reactive with the recombinant peptide of this invention may be obtained in a number of ways which will be readily apparent to those skilled in the art (see, e.g.) Sanbrook et al.). Sera from chickens suffering from coceidiosis may be used as a source of antibodies. Purification of the antibodies can be accomplished by selective binding from the serum, for instance by using cells transformed with a DNA sequence recovered from the unique lambda gt11 EcoRI site of the bacteriophage identified by ATCC Accession No. 68450. Alternatively, the recombinant protein, obtained as described above can be injected into an animal as an immunogen to elicit polyclonal antibody production. The resultant polyclonal antisera may be used directly or purified as described.

In another alternative, monoclonal antibodies specifically immunoreactive with the protein may be prepared according to well known methods (See, e.g., Kohler and Milstein, 1976, Eur. J. Immunol., 6:611), using the peptide of this invention as an immunogen, using it for selection or using it for both functions. These and other methods for preparing antibodies that are specifically immunoreactive with the recombinant protein of this invention are easily within the skill of the ordinary worker in the art.

Recombinant Anticoccidial Vaccine

A vaccine composition containing the recombinant peptide may be prepared for use by standard methods, well known to those of ordinary skill in the art. In one embodiment, the immunogenic peptide may be produced in a recombinant system by expression of the DNA sequence provided by this invention and subsequently isolated. For example, microbial cells containing the exogenous gene of interest may be cultured in large volume bioreactors, then collected by centrifugation and subsequently ruptured, for instance by high pressure homogenization. The resulting cell lysate may be resuspended in appropriate diluent (such as those used in the Examples) and filtered to obtain an aqueous suspension of the immunogen. The recombinant protein can be administered in crude form, for example, by diluting in a 0.1M phosphate buffer (pH 7.4) to 50-500 ug/ml concentration, and then passing through a sterile 0.22 micron filter.

Preferably the crude protein preparation is enriched for the recombinant protein before administration by preparative ion exchange chromatography, affinity chromatography or other preparative extraction technique. Additional chromatographic purification and concentration steps may be performed as required including column chromatography and gel electrophoresis. Especially preferred is purification using an affinity column comprising immobilized antibodies from the sera of chickens with coccidiosis. System conditions of temperature, pH, oxygen saturation and nutrient requirements depend on specific equipment and cell types used; optimal conditions are easily determined by routine experimentation, This procedure will provide large quantities of recombinant protein for therapeutic evaluation and use, Methods of preparing and administering recombinant peptide immunogens are also taught in European Patent Publication No. 0 344 808, which is incorporated herein by reference, The vaccine of this invention may be used to protect the chicken (*Gallus domesticus*) against coccidiosis, The vaccine may be administered by well known methods; for example aqueous solutions of the vaccine with or without adjuvant may be administered by intramuscular or subcutaneous injection or by intraperitoneal injection.

Alternatively, the vaccine may be a "live vaccine," where the DNA sequence encoding the peptide immunogen is inserted in a viral genome such as fowl pox virus and the modified virus is used to infect the chicken population targeted for protection. The methods for preparing and administering such a "live" vaccine are taught in International Patent Application PCT/US89/02918, which is incorporated herein by reference (See, inter alia, p. 6). Another "live vaccine" method uses normal gut flora, transformed with DNA encoding the desired peptide immunogen and administered to the target population, as taught in European Patent Publication No. 0 324 648, which is incorporated herein by reference.

This invention does not contemplate vaccine compositions comprising whole Eimeria cells, whether live or "killed cells," because such vaccines carry a risk of infecting the bird by residual virulent Eimeria cells. Rather, the vaccines of this invention contain one or more immunogenic peptides which are cross-reactive with Eimeria proteins, while being substantially free of other Eimeria proteins. Because the proteins on the surface of Eimeria cells are most easily accessible to the antibodies generated through immunization, one preferred embodiment is a vaccine comprising a peptides cross reactive with a cell surface protein of Eimeria, but substantially free of all non-surface Eimeria proteins.

This invention also contemplates a vaccine containing more than one immunogen. Such a vaccine will contain two or more distinct peptides which are cross-reactive, respectively, with epitopes on different proteins found on the surface of cells of Eimeria species. Preferably each of the distinct peptides are each cross-reactive with surface proteins from at least one different Eimeria species. Most preferably, at least one of immunogenic peptides is cross-reactive with the peptide encoded by the recombinant DNA sequence of rBP1-2, because that peptide cross-reacts with surface proteins found on a number of different Eimeria species.

The following examples are provided to illustrate the invention, but are not intended to limit the scope of the invention, which is limited only by the claims.

EXAMPLE 1

Antiserum Preparation

Specific-pathogen-free birds were each given approximately 50,000-75,000 sporulated *E. maxima* oocysts per os (orally). On the 14th day post-challenge, 5 cc of whole blood was obtained by brachial venapuncture from each bird. The blood was pooled and the hyperimmune serum separated by incubating the blood at 37 C. for 30-45 minutes, cooling at 4 C. for 60 minutes, and then centrifuging at 3000 rpm×10 minutes. Lipids were removed from the serum by combining equal volumes of serum and Lipid Clearing Solution (Beckman Company, Fullerton, Calif.), and vortexing for 10 seconds. The liquid was then centrifuged for 5 minutes at 3000 rpm, and the delipidized upper layer collected by aspiration and diluted 1:1 with binding buffer. The antibody was then extracted using a recombinant protein A purification kit (Beckman Company, Fullerton, Calif.) according to the manufacturer's protocol. The diluted serum was delivered onto a recombinant protein A column, allowed to drain and then washed with 10 ml binding buffer. The rec-protein A column was then placed into the barrel of a buffer exchange column and five ml of elution buffer was added to the tee-protein A column, allowing 0.5 to 1.0 ml eluent fractions to be collected. Additional amounts of exchange buffer (0.1M saline) were passed through the column apparatus to completely elute the antibody. Fractions containing the antibody were identified by spectrophotometric absorbance at 280 nm. The appropriate fractions were then pooled and concentrated by sample concentration columns in the kit. Typical protein concentrations at this point ranged from 0.5-2.0 mg/ml.

Removal of Antibodies Specific for *E. coli* Antigens

Antibodies reactive with *E. coli* were adsorbed using the technique of Sambrook et al., (1989). A non-transformed colony of *E. coli* Y1090 was inoculated into 10 ml of sterile LB media and allowed to incubate overnight at 37 C. The following morning the bacterial cells were collected by centrifugation, and resuspended in 500 ul sterile distilled water. The cells were disrupted by 4-5 freeze/thaw cycles using dry ice and 37 C. water. They were then immersed in wet ice and sonicated (30 seconds on, 30 seconds off) 4-5 times. The 500 ul of crude lysate was then added to 1000 ul antibody an allowed to incubate at room temperature for 4 hours. Following the incubation, the antibody solution was centrifuged at 10,000 rpm×10 minutes. The supernatant was then stored at 0 C. for future use.

EXAMPLE 2

Preparation of an Anticoccidial Immunogen Oocyst Preparation

Specific-pathogen-free birds were placed in a battery brooder for collection of oocyst according to the method of Norton (1989) with slight modification. On day I the birds were given a challenge dose of the appropriate Eimeria species (for efficacy challenges: a mixture of *E. tenella, E. mitis, E. acervulina, E. maxima, E. praecox,* and *E. brunetti*; for nucleic acid extraction, *E. maxima*) mixed in 10 grams of feed per 6 birds. On days 4-6 the feces from the birds was collected in a stainless steel pan containing 2% potassium dichromate. Following the collection period, the feces was stirred with a slow propellor homogenizer for 15 minutes, creating a pourable slurry This was then passed through a double layer of cheesecloth. The filtrate was centrifuged at 1600 rpm×10 minutes. The supernatant was discarded, and the pellet was resuspended in 2.2M sucrose and recentrifuged. The floating layer after centrifugation was siphoned off and reserved. The remaining pellet was resuspended and again centrifuged. The second floating layer was siphoned and combined with the first floating layer. This was diluted with water (3 parts oocyst layer to 7 parts tap water) and centrifuged at 3000 rpm×10 minutes. The oocyst pellet was resuspended in 100 ml water, and quantified using a McMaster's chamber slide (Olympic Equine Products, Issaquah, Wash.). The 100 ml suspension was then sporulated with agitation and aeration on an America V rotator American Hospital Supply Corporation, Miami, Fla.) at 140 rpm for 64–72 hours.

mRNA Extraction and Purification

RNA was extracted and purified according to the method of Sambrook et al., (1989). The sporulated *E. maxima* oocysts were collected by centrifugation, rinsed twice in cold saline, and then resuspended by briefly vortexing in 200 ul RNA extraction buffer (0.14M NaCl, 1.5 mM MgCl2, 10 mM TRIS-HCl (pH 8.6), 0.5% Nonidet-40, 1 mM dithithreitol, 20 mM vanadyl ribonueleoside complexes). The oocyst were then disaggregated by vortexing 3 interrupted minutes with acid-washed glass beads followed by alternate freeze/-thaw cycles to release the cytosol. Cellular debris was removed by centrifugation in a microcentrifuge tube at 5000 rpm×2–3 minutes. To the supernatant was added 200 ul of proteinase digestion buffer (0.3M TRIS-HCl, pH 8.0, 25 mM EDTA, pH 8.0, 0.3M NaCl, and 2% SDS) and proteinase K (final conc. 50 ug/ml). The tube was gently vortexed to mix, then incubated for 30 minutes at 37 C. The proteins were removed by extracting once with an equal volume of phenol-chloroform, and the aqueous phase collected by centrifugation at 5000 g×10 minutes. The aqueous phase was then transferred to a fresh microfuge tube and combined with 400 ul ice-cold isopropanol, mixed well and incubated on wet ice for 30 minutes. The RNA was collected by centrifugation at 15,000 rpm×10 minutes. The supernatant was aspirated and the pellet washed with 1 ml of ethanol, and then recentrifuged. The pellet was then dried in the open tube at room temperature until all the ethanol had evaporated. The pellet was resuspended in 200 ul 50 mM TRIS-HCl and 1 mM EDTA (pH 8.0) containing 10mM MgCl2, 0.1 mM dithiothreitol and ug/ml RNase-free pancreatic DNase. After incubating 60 minutes at 37 C., EDTA and SDS were added to final concentrations of 10 mM and 0.29% respectively. The solution was extracted once with an equal volume of phenol:-chloroform. The aqueous layer was separated by centrifugation at 15,000 rpm×5 minutes, transferred to a fresh tube and combined with 0.1 volume 3M sodium acetate (final concentration 0.3M) and 2.5 volumes ice-cold ethanol, and allowed to remain on wet ice for 30 minutes. The RNA was collected again by centrifugation at 15,000 rpm×5 minutes, and then allowed to air dry in an open tube until the ethanol was evaporated. The pellet was resuspended in 200 ul TE (pH 7.6) combined with 500 ul ethanol, and then stored at −70 C. until needed for further purification.

From the crude nucleic acid extract, mRNA was isolated through the use of an oligo (dT) cellulose column. The column was prepared by mixing a 2 ml slurry of oligo (dT) cellulose and loading buffer (20 mM Tris, pH 7.4, 0.1M NaCl, 1 mM EDTA, 0.1% SDS) and pouring into a sterile 5 ml syringe barrel containing 0.5 inches glass wool packing. The slurry was then washed with 3 ml of 0.1M NaOH and 5 mM EDTA. The column was next washed with sterile water until the pH of the eluent was leas than 8.0, and finally equilibrated with 5 ml of equilibration buffer (40 mM TRIS, pH 7.4, 1 mM NaCl, 1 mM EDTA, 0.1% SDS). The dissolved RNA was heated to 65 C. for 5 minutes, then combined with prewarmed (65 C.) loading buffer (40 mM TRIS, pH 7.4, 1M NaCl, 1 mM EDTA, 0.1% SDS), mixed and allowed to cool for 2 minutes. The sample was then applied to the oligo (dT) column. The eluate was collected and heated to 65 C. for another 5 minutes, then allowed to cool for 2 minutes. The eluate was then reapplied to the column, and followed with 5 ml of loading buffer (20 mM TRIS, pH 7.4, 0.1M NaCl, 1 mM EDTA, 0.1% SDS). The resulting eluate, containing nonpoly(A+) RNA, was discarded. Elution buffer (1.5 ml of 10 mM TRIS, pH 7.4, 1 mM EDTA, 0.05% SDS) was next added to the column, and 10 drop fractions were collected. The RNA-containing fractions were identified by spotting 2 ul drops of each column sample onto ethidium bromide/agarose plates, and illuminating after 20 minutes with short-wave length ultraviolet light. The appropriate sample fractions were purified and concentrated by pooling all positive fractions, and adding 1/10th volume 3M sodium acetate (pH 6.0) and 2.5 volumes ethanol. The solution was then incubated on dry ice for 30 minutes and centrifuged at 10,000 rpm×10 minutes. The resulting pellet was washed with 80% ethanol, dried under vacuum desiccation for 15 minutes, and resuspended in sterile, autoclaved water at a concentration of approximately 1 ug/ul. The mRNA was stored at −70 C. until used for cDNA synthesis.

cDNA Synthesis

The cDNA was synthesized using a cDNA Synthesis System (Bethesda Research Laboratories, Gaithersburg, Md.) according to the manufacturer's protocol. In a sterile diethylpyrocarbonate (DEPC)-treated microcentrifuge tube, 10 ul of reaction buffer (250 mM TRIS-HCl, pH 8.3, 375 mM KCl, 15 mM MgCl2, 50 mM dithiothreitol) was combined with 2.5 ul 10 mM dNTP (500 umoles each of dATP, dCTP. dGTP, and dTTP), 5 ul oligo (dT), 10 ul mRNA, 20 ul DEPC-treated water, and 2.5 ul M-MLV reverse transcriptase and placed in 37 C. incubation for 1 hour, then placed on wet ice. To this reaction mixture was added 288.25 ul DEPC-treated water, 10 mM dNTP mix. 40 ul second strand buffer (188 mM TRIS-HCl, pH 8.3, 906 mM KCl. 100 mM ammonium sulfate, 46 mM MgCl2, 37.5 mM dithiothreitol, and 1.5 mM NAD), 10 ul *E. coli* DNA polymerase I, 1.75 ul RNAse H, and 1.25 ul *E. coli* DNA ligase. The microcentrifuge tube was then vortexed gently to mix, and then incubated at 16 C. for a period of 2 hours. Following the incubation the reaction mixture was kept on wet ice, then extracted with phenol/chloroform, and reprecipitated from ammonium acetate with ethanol. The cDNA was then lightly digested with EcoRI to obtain cohesive termini by adding 1 ul of 10×buffer (0.5M NaCl, 1M TRIS, pH 7.4, 0.1M MgCl2) 1 ul cDNA (0.5 ug), 1 ul EcoRI, and 7 ul sterile water, and incubating 20–30 minutes at 37 C.

Ligation and Packaging into Lambda gt11 Arms

One microgram of commercially-obtained lambda gt11 DNA, (Lambda gt11 Cloning System, Bethesda Research Laboratories. Gaithersburg, Md.) previously digested with EcoRI and dephosphorylated, was combined with 0.2 ug cDNA in a 10 ul reaction mixture containing 50 mM TRIS-HCl (pH 7.5), 10 mM MgCl2, 10 mM DTT, and 1.5 mM ATP according to the manufacturer's protocol. One unit of T4 DNA ligase was then added, and the mixture allowed to incubate overnight at 4 C. The ligated DNA was then packaged by combining with lambda lysogen DNA packaging extracts at 20 C. for 2 hours, then adding 0.5 ml phage dilution buffer (50 Mm TRIS-HCl pH 7.5, 100 mM NaCl, 10 mM MgCl2, 0.01% gelatin) and 20 ul chloroform for 10 minutes. The packaged phage was then stored at 4 C.

Plating Cells

Sterile Luria Bertani media (100 ml) containing 2 ml malrose solution (20% w/v) was inoculated with a fresh colony of *E. coli* Y1088 plating cells in a sterile 500 ml flask, and allowed to grow overnight. The cells were collected by centrifugation at 2500 g×10 minutes in sterile tubes. The superantant was decanted, and each pellet resuspended in 25 ml sterile 10 mM MgSO4.

The in vitro packaging reactions from above were diluted to low (10 ul phage, 90 ul phage dilution buffer), medium (50 ul phage and 50 ul PDB) and high (75 ul phage, 25 ul PDB) titers, and separately coincubated with 200 ul Y1088 cells for 30 minutes at 37 C. The cells and phage were then combined with 3 ml of molten top agar, swirled. and poured onto LB/ampicillin plates. Once the top agar was set, the plates were inverted and incubated overnight at 42 C. The next morning, recombinant phage were selected from clear plaques and removed in plugs from the agar by stabbing with the tip of a blunt, sterile 14 gauge needle. The plugs were resuspended in 100 ul water and 1 drop of chloroform, vortexed briefly, and allowed to incubate room temperature with intermittent vortexing for 30 minutes. The released phage were then added to 200 ul Y1090 cells, and allowed to incubate at 37 C. for 30 minutes. The Y1090/phage complex was then added to 3 ml of molten top agar containing 10 mM MgCl, ul of 100 mM IPTG and 9 ul of 10% X-Gal, and plated onto LB agar containing ampicillin (50 ug/ml). The top agar was allowed to harden for 15 minutes, then inverted and allowed to incubate overnight at 42 C. The recombinant colonies were evidenced by clear or white plaques on the bacterial lawn. Non-recombinant plaques were bluish-green in color.

Screening Plated Library for Positive Clones

Positive clones were screened and identified according to the technique of Davis et al. (1986) and Sambrook et al. (1989). The agar plate covers were removed, and the plates placed agar side down on a sterile surface and allowed to air dry for 30 minutes. Nitrocellulose filters were placed on the agar, and the covers replaced. The filters were then allowed to stay in place approximately 16 hours. They were then gently removed with flat-faced forceps and allowed to dry for 30 minutes at room temperature. The filter was then exposed to chloroform vapor for 10–15 minutes, then again allowed to dry 30 minutes. The filter was next washed twice in TBST (TRIS-buffered saline with 0.005% Tween-20), 10 minutes per wash. The filter was then incubated in blocking solution (3% (w/v) bovine serum albumin, fraction 5 in 0.1M TRIS-HCl, pH 7.5, 0.15M NaCl) for 1 hour at room temperature with gentle agitation. A 100 ul aliquot of anti-coccidial antibody, purified as described in Example 1, was added to each 10 ml of the blocking bath, and the incubation was continued for an additional 60 minutes. The filter was then washed 4 times in TBST, 5 minutes per wash. Next the filter was incubated in blocking solution containing alkaline phosphatase-conjugated anti-chicken IgG (10 ul IgG in 10 ml blocking solution) for I hour at room temperature. This was followed by one wash in TRIS-buffered saline for 5 minutes, and air drying on a clean filter paper. Color development solution was prepared by adding 40 ul nitroblue tetrazolium (NBT) and 30 u 5-bromo-4-chloro-3-indoylphosphate (BCIP) to color development stock solution 0.1M TRIS-HCl, pH 9.5, 0.1M sodium chloride, 50 mM MgCl2). The filter was placed in this solution in the dark for 30 minutes, then rinsed in TBS and placed in stop solution for 60 seconds. and allowed to air dry. The recombinant bacterial colonies synthesizing the anti-coccidial protein were noted by the development of purple-colored dots on the nitrocellulose membrane.

Colony Selection and Amplification

Clear plaques evidencing color development on the immunoblot screening procedure were selected for further study. The corresponding plaque regions on the original plate were located, and samples removed from each selected plaque by sterile needle aspiration. These plugs were dissolved, lysed with a drop of chloroform and used to infect cultures of *E. coli* Y1090 as described previously. Each subsequent cell line was designated according the original experimental trial and plaque number. Selected colonies were amplified in LB broth containing ampicillin. Upon establishing this crude library, the transformed cells were maintained in LB broth and 40% glycerol (1:1) at −20 C.

Alternatively, the cDNA may be initially inserted into a plasmid such as pBR322 to link the selective markers amp or tet to the DNA, and then attached to the lambda gill arms as described above, if care is used not to exceed the packaging capacity of the phage.

Separate clones were isolated from a lamda gt11 library, a pBR322 library, and a pTRP56 library grown in *S. cerivisiae*. A clone obtained from the recombinant lambda bacteriophage gt11 library, and referred to as rBP1-2, was deposited as ATCC 68450. A clone designated rPV1-89 was selected from the pBR322 library and deposited as ATCC No. 68537.

The cloned cDNA gene has three EcoRI restriction sites, and is approximately 4–7 kilobases in length. While this invention, in a preferred embodiment, contemplates immunogenic peptides encoded by the entire sequence isolated from Eimeria, immunogenic peptides encoded by fragments of the sequence are also contemplated, such as one or more of the EcoRI fragments of rBP1-2. In particular, DNA sequences which include the sequence of the 2 kilobase EcoRI fragment from the center of the rBP1-2 sequence are contemplated.

ATCC Recombinant Cell Patent Deposit

A 100 ul aliquot of recombinant *E. coli* Y1090/rBP1-2 cells was allowed to grow overnight in 500 ml fresh Luria Bertani media containing 50 ug/ml ampicillin at 37 C. The following morning the cells were collected by centrifugation, resuspended in 200 ml of a sterile 5% skim milk (Difco Laboratories, Detroit, MI) and 0.25% bactopeptone (Difco Laboratories, Detroit, Mich.) lyophilization resuspension media, and lyophilized (Engler, 1990). The culture was then deposited with the American Type Culture Collection, 12301 Parklawn Dr., Rockville, Md. 20852, U.S.A., effective Oct. 26, 1990. The assigned deposit number is ATCC Accession No. 68450. *E. coli* HB101/rPV1-89 cells were grown in a similar fashion and deposited on Mar. 1, 1991. This deposit was assigned ATCC Accession No. 68537.

EXAMPLE 3

Recombinant Protein Isolation

Recombinant proteins were isolated according to the technique of Becker et al., (1990) with minor modifications. The recombinant *E. coli* Y1090/rBP1-2 cells were allowed to grow overnight at 37 degrees C. in sterile, sealed 1000 ml Ehrlenmeyer flasks containing 500 ml Luria Bertani broth and ampicillin (50 ug/ml). The bacterial cells were pelleted by centrifugation and resuspended in 5–10 ml Z buffer (0.12M Na2HPO4, 0.4M Na2H2PO4, 0.01M KCl, 1 mM MgSO4. and 0.3 (v/v) 2-mercaptoethanol, pH 7.0) to which 0.174 mg phenylmethylsulfonyl fluoride (PMSF)/ml had been added. An equivalent amount of acid-washed glass beads was added to the tube. The cells were then vortexed at high speed for 30 seconds followed by immersion in ice water for 30 seconds to prevent overhearing. This process was repeated for a total of 6 cycles. The glass beads were allowed to settle to the bottom of the tube and the liquid was aspirated and transferred into a clean vessel. Using a Vibra-Cell sonicator (Sonics and Materials Incorporated, Danbury, Conn.) the lysate was then sonicated for 30 seconds×50 watts on wet ice, allowed to rest 30 seconds, then repeated 2 more times. This was then centrifuged at 5000 rpm×5 minutes and the pellet discarded. The supernarant was then added to 100 ml of fresh Z-buffer in a clean 250 ml glass beaker resting in an ice bath atop a magnetic rotary mixer. Another 17.4 mg of PMSF was added to the liquid, and stirred at slow to moderate speed. The recombinant protein was then precipitated from the crude lysate by addition of ammonium sulfate to a final concentration of 70% saturation. The lysate and ammonium sulfate was allowed to stir for 1–2 hours in wet ice. The resulting precipitate was collected by centrifugation, and resuspended in a small volume of 0.1M sodium phosphate buffer, pH 7.4. Typical resuspension protein concentrations at this step were 500–700 ug/ml as determined using a Bio-Rad colorimetric protein micro-assay (Bio-Rad Laboratories, Richmond, Calif.). A similar procedure may be used to obtain recombinant peptide from cells transformed with rPV1-89.

Specific immunogenic fractions were obtained by standard ion exchange or gel permeation liquid chromatography techniques. The fractions were identified by their immunoreactivity with serum of chickens challenged with *E. maxima* as described. Recombinant proteins encoded by both rBP1-2 and rPV1-89 show the same immunoreactivity patterns with sera from different chickens.

EXAMPLES 4

Recombinant Protein Characterization

Molecular weight of the recombinant proteins was determined by SDS-PAGE (11–23% exponential gradient gel, 6% stacking gel, anolyte buffer: 1.2M ammediol sulfate, pH 9.5; catholyte buffer: 0.75M ammediol, 0.75M glycine, pH 9.5 plus 0.5% sodium dodecyl sulfate: running conditions: 50 volts×15 minutes then 100 volts×6 hours). Gels of the crude protein extract from cells transformed with rPV1-89 contained a band at 45–65 kD that was absent in gels of the untransformed host strain. Gels of the crude protein extract from cells transformed with rBP1-2 had a similar band representing the fusion protein at about 140 kD; by subtracting the weight due to the portion of the fusion protein contributed by the beta-galactosidase gene, the molecular weight of the Eimeria peptide can be calculated to be approximately 50–65 kilodaltons. The protein itself is highly stable at 4 C. for up to sixty days in Z buffer (described above), but loses appreciable activity (near 100%) upon dialysis against 0.1M sodium cloloride.

Fractional protein concentrations were determined from total protein concentrations by high pressure liquid chromatography (conditions: diethylaminoethyl (DEAE) column; buffer 1:20 mM TRIS, pH 8.5; buffer 2:20 mM TRIS, pH 7.0 and 0.3M sodium chloride: linear gradient: 0–100% buffer 2, 30 minutes; flow rate 1.0 ml/minute at 280 nm, 0.5 AUFS). Major bacterial proteins generally eluted at run times from 2.5–3.5 minutes. The recombinant fusion proteins eluted in 2 major peaks at 14.4- and 16.8-minute run times. The recombinant doublet peaks typically accounted for approximately 24 percent of the total protein concentration for rBP1-2 protein samples and approximately 10 percent for rPV1-89 protein samples. In crude protein fractions from cells transformed with another pBR322 vector, designated rPV1-12, recombinant protein represented approximately 5 percent of the total.

EXAMPLE 5

Recombinant Protein Sequence

The peptide expressed from the expression vector rPV1-89is not a fusion protein, and therefore Eimeria sequences rather than *E. coli* sequences code for the amino terminal portion. The rPV1-89 peptide was obtained by transforming *E. coli* cells with rPV1-89 and selecting a transformant that reacted with the partially purified antisera of Example 1. The selected transformant was cultured, and crude protein extract from the culture was separated by SDS-PAGE. The band which appeared in extracts of the transformant but not in extracts of the untransformed host was excised from the gel and the protein was electroeluted to obtain a purified preparation of the recombinant protein. Sequence analysis of the amino terminus of the recombinant protein was carried out using an Applied Biosystems Incorporated Model 477A Protein Sequenator. The results of sequence analysis are shown in Table 1, and the amino acid sequence, as determined, is provided in SEQ ID No: 1.

TABLE 1

| Cycle | N Terminal Sequence | | Yield (picomoles) |
|---|---|---|---|
| | Residue | | |
| 1 | X | X | — |
| 2 | E | Glu | 1.77 |
| 3 | Q | Gln | 3.25 |
| 4 | E | Glu | 2.73 |
| 5 | T | Thr | 0.42 |
| 6 | S | Ser | 1.12 |
| 7 | A | Ala | 1.76 |
| 8 | T | Thr | 0.56 |
| 9 | E | Glu | 2.95 |
| 10 | V | Val | 0.19 |
| 11 | X | X | — |
| 12 | T | Thr | 0.59 |
| 13 | P | Pro | 0.73 |
| 14 | S | Ser | 0.83 |
| 15 | Y | Tyr | 0.37 |
| 16 | K | Lys | 0.17 |
| 17 | M | Met | 0.22 |
| 18 | T | Thr | 0.45 |
| 19 | X | X | — |
| 20 | S | Ser | 0.57 |

The sequence disclosed in Table 1 does not appear in *E. coli* beta-galactosidase. The sequence was compared to the first 20 amino acids of the proteins disclosed by the various authors who report anti-coccidial vaccine preparations (Table 2). The comparison showed a maximum homology of 3 residues out of 20. Thus, the peptide of this invention is unique among peptides isolated from clones of Eimeria DNA.

TABLE 2

Comparison of sequence homology among the amino terminus of selected recombinant proteins with rPV1-89 protein

| Author | Number of matching residues per amino terminus | Percent homology |
|---|---|---|
| Miller, 1989 | 0/20 | 0 |
| AU-A28542/89 (Merck) | 3/20 | 15 |
| EP 0 324 648 (Merck) | 1/20 | 5 |
| AU-A65869/86 (Solvay and Cie) | 0/20 | 0 |
| WO 0 349 071 (Genex) | 2/20 | 10 |
| EP 0 349 071 (Akzo) | 1/20 | 5 |
| EP 0 344 808 (1) (Hoffman) | 1/20 | 5 |
| EP 0 344 808 (2) (Hoffman) | 1/20 | 5 |
| EP 0 344 808 (3) (Hoffman) | 2/20 | 10 |
| EP 0 344 808 (4) (Hoffman) | 0/20 | 0 |

EXAMPLE 6

Initial In Vivo Efficacy Trials

As an initial study, a small sample size (n=27) was used to study potential toxicities of the vaccine, and to determine the capability of the recombinant protein to inhibit oocyst proliferation and to reduce intestinal lesions against a mild challenge (10,000 oocysts/bird). The birds were specific-pathogen-free Leghorns, of mixed sex, that had been reared under isolation until 4 weeks of age. The birds were arbitrarily assigned to the two treatments. The vaccine group was given 150 ug recombinant protein in a mixture of phosphate buffered saline and incomplete Freund's adjuvant (5:1) (total injection volume 1.0 ml/bird) intramuscularly in a single site. The injection was repeated in 7 days in a matching contralateral site. In another 7 days the birds were given an oral dose of E. maxima oocysts (10,000/bird). At 7 days post-challenge the birds were necropsied, and the intestines examined for evidence of lesions. Results of the study are indicated in Table 3.

TABLE 3

Results of Initial Efficacy Trial

| Group | treatment | n | mean body weight | mean lesion scores | oocyst[a] count per gram |
|---|---|---|---|---|---|
| 1 | non-injected control | 13 | 1432.92 | 3.00 | 1.91 |
| 2 | recombinant protein | 14 | 1467.50 | 2.58 | 0.69 |

[a]oocysts × $10^6$ per gram of feces removed from intestine and cecae.

EXAMPLE 7

In Vivo Efficacy Trial 2

In the second trial the sample size was expanded to n=300, and conditions were established to simulate an actual production environment. The test was conducted in a commercial poultry house with individual floor pens, with concrete floors and rice hull litter. Ross × Arbor Acres broiler chicks were obtained from a commercial hatchery at one day of age (mixed sex, random distribution), and randomly assigned to one of six floor pens at a placement density of one square foot per bird. All birds were provided non-medicated broiler feed (prestarter, starter, grower, and finisher) and water ad libitum. Two replicates of each treatment were randomly assigned among the six pens (see Table 4). Vaccination was carried out according to the schedule shown in Table 5.

TABLE 4

Pen and treatment assignments: Trial 2

| Treatment | Pen number | n |
|---|---|---|
| non-injected control | 4, 6 | 50/pen |
| beta-galactosidase | 2, 5 | 50/pen |
| recombinant protein rBP1-2 | 1, 3 | 50/pen |

TABLE 5

Vaccination Schedule and Dosage: Trial 2

| Treatment | Dosage/route | Day |
|---|---|---|
| control | — | — |
| beta-galactosidase | 50 ug/sub-q | 1 |
|  | 50 ug/sub-q | 7 |
|  | 50 ug/sub-q | 21 |
| recombinant protein rBP1-2 | 10 ug/sub-q | 1 |
|  | 50 ug/sub-q | 7 |
|  | 100 ug/sub-q | 21 |

On day 28, each replicate of birds was challenged with a mixed culture (E. tenella, E. mitis, E. acervulina, E. maxima, E. praecox, and E. brunetti) of 50,000 oocysts/bird, diluted in crumbled feed (83.3 grams feed per 50 birds). At 7 days post challenge (day 35), the birds were euthanized and examined for the presence of intestinal lesions according to the method of Johnson and Reid (1970). Lesion scores, feed conversion, body weights, and oocyst counts per gram of feces were obtained and are reported in Table 6.

TABLE 6

Results of Efficacy Trial 2

|  | Control | Beta-galactosidase | Recombinant vaccine |
|---|---|---|---|
| live weight (grams) | 1405.75 (a)[1] | 1335.03 (b) | 1418.33 (a) |
| feed conversion[2] | 1.68 | 1.87 | 1.78 |
| percent coccidial mortality | 0 | 0 | 0 |
| lesion score | 2.563 (a) | 2.711 (a) | 2.279 (b) |
| oocyst count[3] | 1.541 (a) | 1.446 (a) | 0.847 (b) |
| percent inhibition of oocysts with respect to control | — | 6.10 | 45.0 |

[1]values within rows having different letters vary siqnificantly at probability less than 0.05
[2]adjusted to mean control live weight
[3]oocysts × $10^6$ per gram feces

EXAMPLE 8

In Vivo Efficacy Trial 3

In the third trial, the anticoccidial efficacy of the recombinant vaccine was compared to various commercial coccidiostat shuttle programs in a defined challenge consisting of mixed Arkansas field isolates of six pathogenic strains of Eimeria. Day-old commercial broiler chicks were randomly divided among seven treatments, with four replicates per treatment (n=160/replicate) and placed in floor pens in a conventional broiler house. Treatments are described in Table 7; the vaccination for Group 5 was carried out according to the schedule shown in Table 8.

TABLE 7

Treatment description: Trial 3

| Group | Treatment |
|---|---|
| 1 | Nicarb-Coban |
| 2 | Robenz-Coban |

TABLE 7-continued

Treatment description: Trial 3

| Group | Treatment |
|---|---|
| 3 | Nicarb-BioCox |
| 4 | Infected, non-medicated control |
| 5 | rBP1-2 recombinant vaccine[1] |
| 6 | Nicarb-Coban-Zeolyte |
| 7 | Nicarb-Coban-MicroAid |

[1]rBP1-2 and Rehydragel 20% (v/v) aluminum hydroxide adjuvant

TABLE 8

Recombinant vaccine dosage schedule: Trial 3

| Day | Dosage/Route |
|---|---|
| 1 | 50 ug/subcutaneously |
| 7 | 50 ug/subcutaneously |
| 21 | 50 ug/subcutaneously |

On day 28, each replicate of birds was challenged with a mixed culture of E. tenella, E. mitis, E. acervulina, E. maxima, E. praecox, and E. brunetti in a concentration of 90,000 oocysts/bird dispensed in crumbled feed. At seven days post challenge (day 35), a random sample of 8 birds/replicate (32 birds/treatment) was obtained for evaluation. The average data for these birds are presented in Table 9.

TABLE 9

| Treatment[1] | Anticoccidial efficacy Eimeria | | | |
|---|---|---|---|---|
| | Average Lesion Score | Live Weight at 35 Days | Oocyst[2] Count | % Oocyst[3] Reduction |
| NC | 2.344 | 2.789 | 0.273 | 98.32 |
| RC | 2.250 | 2.990 | 0.356 | 97.82 |
| NB | 2.094 | 2.930 | 0.257 | 98.43 |
| INC | 2.223 | 2.906 | 16.316 | — |
| VAC | 2.063 | 2.955 | 0.441 | 97.30 |
| NCZ | 2.313 | 2.755 | 0.292 | 98.21 |
| NCM | 2.219 | 2.818 | 0.290 | 98.22 |

[1]abbreviations: NC Nicarb, Coban; RC - Robenz, Coban; NB - Nicarb, BioCox; INC - infected, nonmedicated control; VAC - rBP1-2 recombinant vaccine; NCZ - Nicarb, Coban, Zeolyte; NCM - Nicarb, Coban, MicroAcid.
[2]oocysts × 10^6 per gram of intestinal contents.
[3]with respect to the infected, nonmedicated control (INC).

We claim:

1. A substantially pure immunogenic peptide corresponding to a peptide encoded by a DNA sequence, wherein said DNA sequence is contained in a recombinant bacteriophage deposited under ATCC Accession No. 68450. said recombinant bacteriophage consisting of bacteriophage lambda gt11, having a unique EcoRI site, and said DNA sequence, which is inserted at said unique EcoRI site.

2. A substantially pure immunogenic peptide encoded by a DNA sequence, wherein said DNA sequence is contained in a recombinant bactefiophage deposited under ATCC Accession No. 68450, said recombinant bicteriophage consisting of bacteriophage lambda gt11, having a unique EcoRI site, and said DNA Sequence, which is inserted at said unique EcoRI site.

3. A vaccine composition comprising an immunogenic peptide according to claim 1, corresponding to a peptide encoded by a DNA sequence, wherein said DNA sequence is contained in a recombinant bacteriophage deposited under ATCC Accession No. 68450. said recombinant bacteriophage consisting of bacteriophage lambda gt11, having a unique EcoRI site, and said DNA sequence, which is inserted at said unique EcoRI site.

4. A vaccine composition comprising an immunogenic peptide according to claim 2, said peptide being encoded by a DNA sequence, wherein said DNA sequence is contained in a recombinant bacteriophage deposited under ATCC Accession No. 68450, said recombinant bacteriophage consisting of bacteriophage lambda gt11, having a unique EcoRI site, and said DNA sequence, which is inserted at said unique ECoRI site.

5. A method of vaccinating chickens against coccidiosis, comprising administering to a chicken an effective amount of a vaccine composition according to claim 3.

6. A method of vaccinating chickens against coccidiosis, comprising administering to a chicken an effective amount of a vaccine composition according to claim 4.

7. A method of vaccinating chickens according to claim 5, wherein said vaccine composition is administered to a chicken by injection.

8. A method of vaccinating chickens according to claim 6, wherein said vaccine composition is administered to a chicken by injection.

* * * * *

UNITED STATES PATENT AND TRADEMARK OFFICE
CERTIFICATE OF CORRECTION

PATENT NO. : 5,387,414
DATED : February 7, 1995
INVENTOR(S) : David E. Harwood and Glenda Hamby It is certified that error appears in the above-indentified patent and that said Letters Patent is hereby corrected as shown below:

On the title page, the following art should be added:

| | | | | |
|---|---|---|---|---|
| AU-A-65869/86 | - | June 4, 1987 | - | Australia |
| 0 231 537 | - | August 12, 1987 | - | Europe |
| 0 324 648 | - | July 19, 1989 | - | Europe |
| AU-A-28542/89 | - | July 11, 1989 | - | Australia |
| 0 328 253 | - | August 16, 1989 | - | Europe |
| 0 344 808 | - | December 6, 1989 | - | Europe |
| 0 349 071 | - | January 3, 1990 | - | Europe |
| WO 90/00403 | - | January 25, 1990 | - | PCT |
| 0 390 267 | - | October 3, 1990 | - | Europe |

Signed and Sealed this

Fourth Day of June, 1996

*Attest:*

BRUCE LEHMAN

*Attesting Officer*      *Commissioner of Patents and Trademarks*